US00PP32877P2

(12) United States Plant Patent

Manly et al.

(10) Patent No.: US PP32,877 P2
(45) Date of Patent: Mar. 9, 2021

(54) APPLE TREE NAMED, 'REGAL D17-121'

(50) Latin Name: *Malus domestica*
Varietal Denomination: Regal D17-121

(71) Applicant: Regal Fruit International, LLC, Ephrata, WA (US)

(72) Inventors: Neal Manly, Ephrata, WA (US); Kenneth Adams, Ephrata, WA (US)

(73) Assignee: Regal Fruit International, LLC, Ephrata, WA (US)

( * ) Notice: Subject to any disclaimer, the term of this patent is extended or adjusted under 35 U.S.C. 154(b) by 0 days.

(21) Appl. No.: 16/873,297

(22) Filed: Mar. 12, 2020

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418
See application file for complete search history.

*Primary Examiner* — Anne Marie Grunberg
(74) *Attorney, Agent, or Firm* — Lee & Hayes, P.C.

(57) ABSTRACT

A new and distinctive variety of *Malus domestica* apple tree from a controlled cross of Honeycrisp x CO-OP 39 that is distinctly different from its parents and other mid-season apples.

5 Drawing Sheets

Latin name: *Malus domestica.*
Varietal denomination: 'Regal D17-121'.

BACKGROUND

The present invention relates to a novel and distinct variety of apple tree which has been denominated varietally as 'Regal D17-121'. More specifically, the present invention relates to a novel mid-season apple tree that is upright, spreading in growth habit, and considered semi-spur that will tip bear. The novel apple tree produces bi-colored fruit that is mostly blush with occasional blotches, mostly round in shape, considered medium to medium-large, and has a six-month shelf life. The flesh of such fruit is dense and crisp, in the sweet-tart category, and resists browning following cutting.

ORIGIN AND ASEXUAL REPRODUCTION

It has long been recognized that important factors contributing to the success of a new variety of apple tree bearing fresh market fruit are the characteristics of both its growth and fruit. Other significant factors affecting the commercial viability of a new variety of apple include storage characteristics, which are reflected by pomological traits such as fruit pressure, soluble solids, and pH. The new variety of apple tree described herein was derived by the following methodology.

In 2008, the new variety 'Regal D17-121' was derived by a controlled pollination of the variety Honeycrisp (U.S. Plant Pat. No. 7,197) with the pollen from CO-OP 39 (U.S. Plant Pat. No. 16,622). As such, the 'Regal D17-121' is most closely related to the Honeycrisp. In August 2010, 'Regal D17-121' was budded onto M9 rootstock (considered first generation) and in September 2014, first fruit was observed. In April 2016, second-generation trees were grafted, and their fruit was observed in September of 2018. Fruit generated from the second-generation trees have been studied and compared, and it appears that all characteristics of the subsequent asexually reproductive trees remain true to that seen in the original first-generation tree.

SUMMARY OF NEW VARIETY

The 'Regal D17-121' apple tree is characterized as to novelty by its distinctive traits from its parent varieties, CO-OP 39 and Honeycrisp. For example, 'Regal D17-121' matures 14 days after Honeycrisp and 10 days after CO-OP 39. At maturity, 'D17-121' has a pressure of 23.8 pounds, compared to Honeycrisp, which has a pressure of 16.5 pounds. At maturity, 'Regal D17-121' has a brix of 15.4, while Honeycrisp has a brix of 14.8. By way of example, 'Regal D17-121' is upright, spreading in growth habit, and is considered a semi-spur that will tip bear. Fruit at maturity is medium to medium-large in size, mostly blush with occasional blotches, and mostly round in shape. The fruit does not exhibit bitterpit and maintains eating quality following four months in common storage.

BRIEF DESCRIPTION OF DRAWINGS

The accompanying drawings are color photographs of the present variety.

NOT A COMMERCIAL WARRANTY

Figure 1:
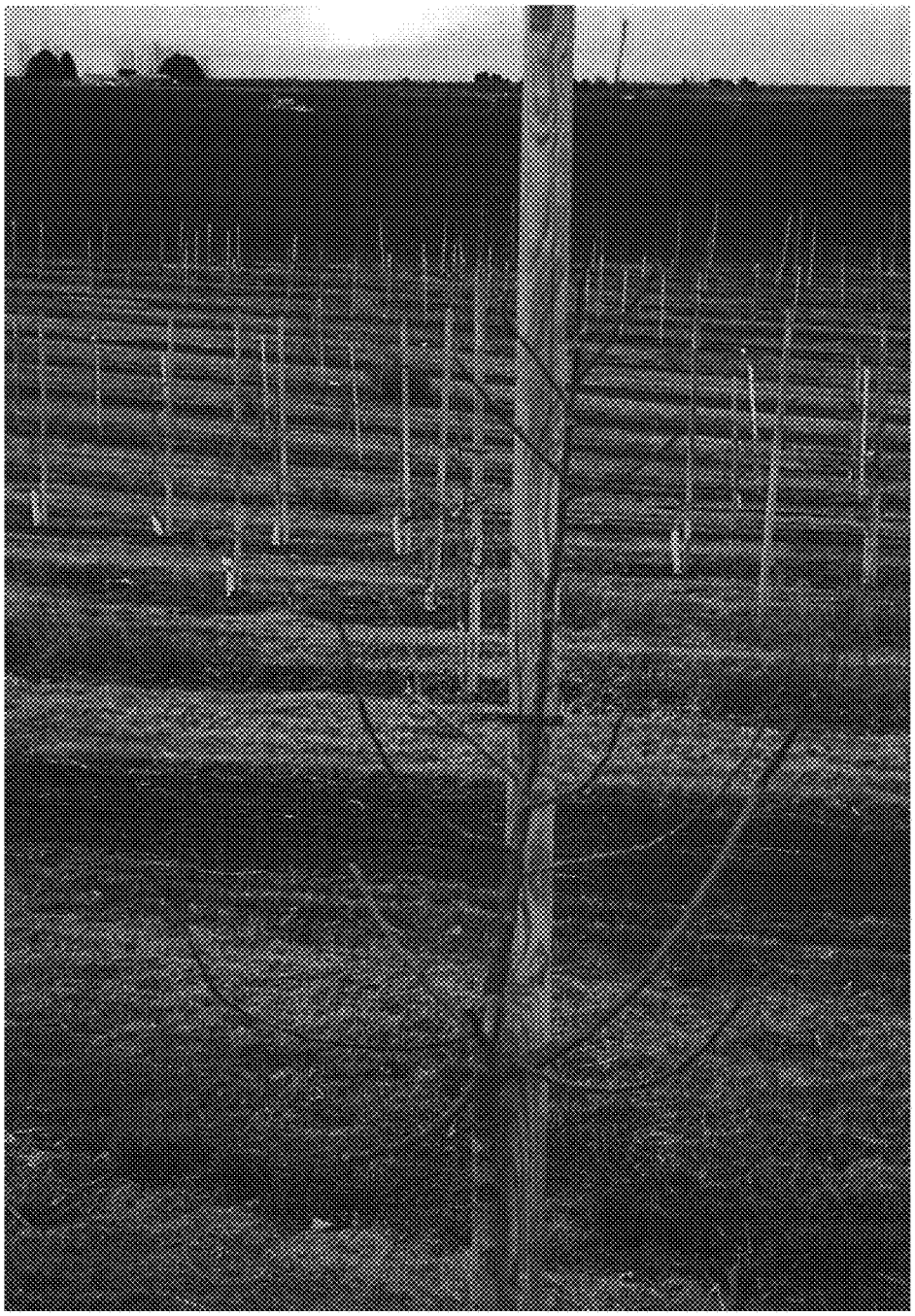
FIG. 1 depicts a three-year-old dormant 'Regal D17-121' tree.
Figure 2:
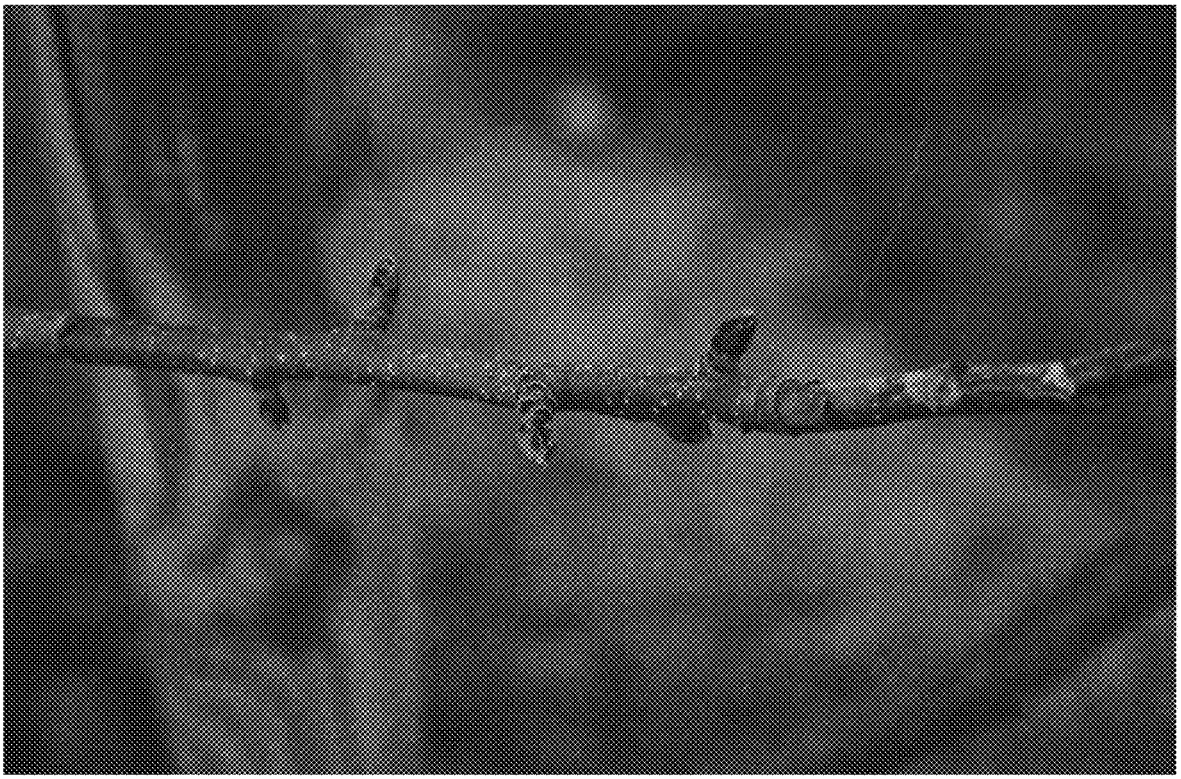
FIG. 2 depicts 'Regal D17-121' spur development.
Figure 3:
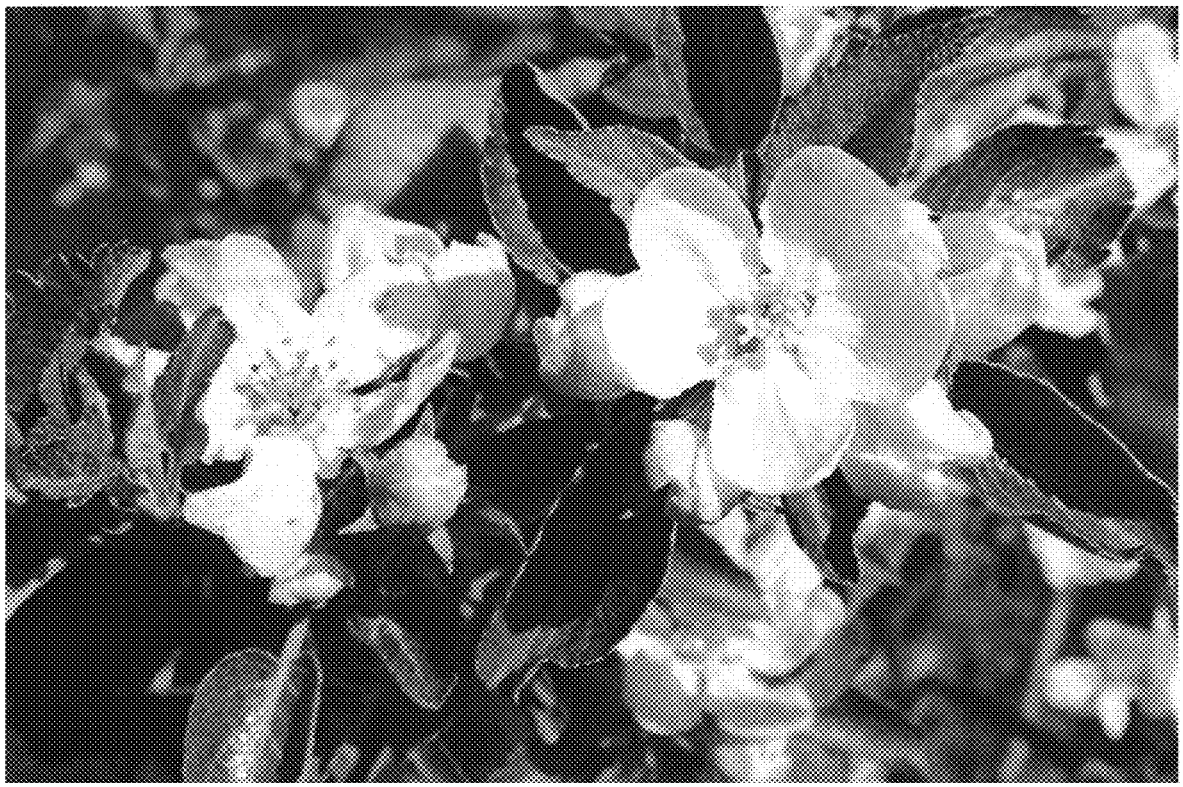
FIG. 3 depicts a typical blossom of 'Regal D17-121' at king bloom.
Figure 4:
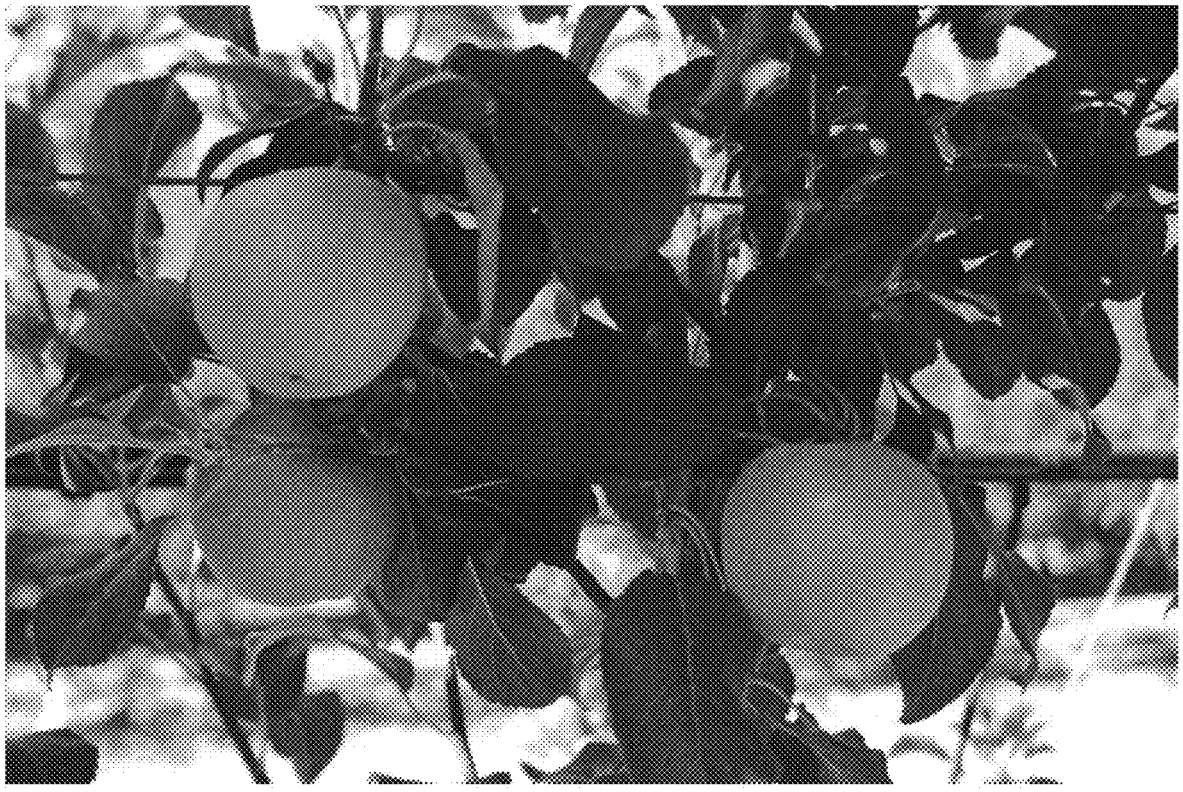
FIG. 4 depicts a fruiting limb of 'Regal D17-121' pre-harvest.
Figure 5:
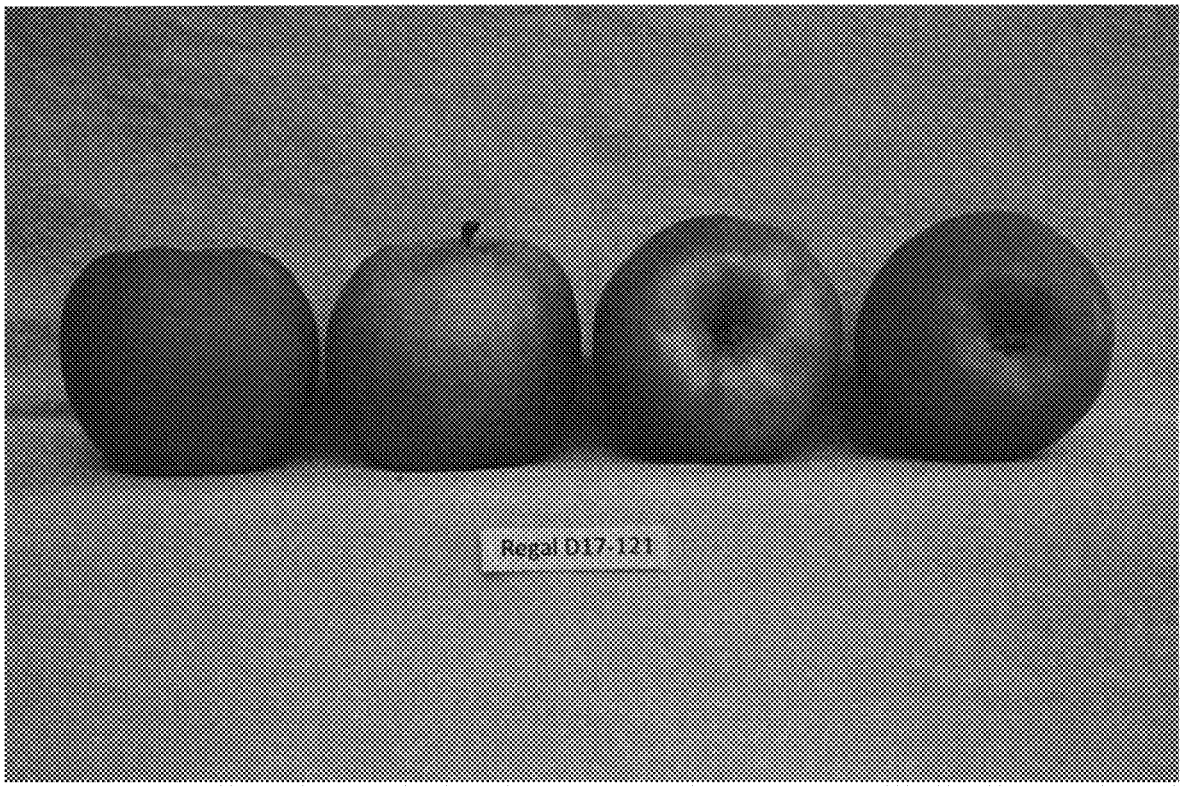
FIG. 5 illustrates four positions of harvest-mature 'Regal D17-121' fruit.

The following detailed description has been prepared to solely comply with the provisions of 35 U.S.C. § 112, and does not constitute a commercial warranty, (either expressed or implied), that the present variety will, in the future, display the botanical, pomological or other characteristics as set forth herein. Therefore, this disclosure may not be relied upon to support any future legal claims, including but not limited to breach of warranty of merchantability, or fitness for any particular purpose, which is directed, in whole, or in part, to the present variety.

DETAILED DESCRIPTION

Referring more specifically to the pomological and botanical details of this new and distinct variety of apple tree, the following has been observed from third-generation trees grown in Vantage, Wash. 98950, USDA Hardiness Zone 7A, and asexually reproduced in Ephrata, Wash., USDA Hardiness Zone 6B. All color references are from The R.H.S. Colour Chart by The Royal Horticulture Society.

The closest known antecedent to 'Regal D17-121' is the Apple Tree named 'Regal D5-100' (U.S. Plant Pat. No. 31,503P3), a variety of *Malus domestica* from a controlled cross of Huaguan x Honeycrisp. The following are some characteristics to distinguish 'Regal D17-121' from 'Regal D5-100'. 'Regal D17-121' is slightly taller and wider than the 'Regal D5-100'. The 'Regal D17-121' leaf is larger, both in length and width, than the leaf of the 'Regal D5-100'. The 'Regal D17-121' produces a larger fruit than that of the 'Regal D5-100'.

Tree:

*Tree type*.—Upright and spreading. Spur type and tip bearer.

*Tree vigor*.—Considered moderate on the high side.

*Tree shape*.—Generally inverted cone.

*Tree height*.—About 10.0 feet.

*Tree width*.—About 4.0 feet.

*Hardiness*.—Considered hardy for the current region grown in.

*Fruit productivity*.—Considered moderate (from about 75 bins to about 80 bins per acre).

Trunk:

*Trunk diameter*.—About 37.9 millimeters when measured at a height of about 30 centimeters above the ground.

*Bark texture*.—Generally smooth.

*Bark color*.—From the Grey-Brown group (RHS N199C).

*Trunk lenticels*.—About eleven per nine square centimeters of growth.

*Trunk lenticel width*.—From about 0.9 millimeters to about 1.9 millimeters.

*Trunk lenticel length*.—From about 2.2 millimeters to about 5.1 millimeters with an average of about 4.2 millimeters.

*Trunk lenticel color*.—From the Yellow-White group (RHS 158D).

*Trunk lenticel shape*.—Generally flat.

Branches:

Scaffold branches:

*Scaffold branch diameter*.—From about 10.8 millimeters to about 14.8 millimeters with an average of about 13.3 millimeters as measured at 10 centimeters from trunk.

*Scaffold branch color*.—From the Greyed-Brown group (RHS N199D).

*Scaffold branch texture*.—Generally smooth.

*Scaffold branch angle*.—About 80 degrees to about 90 degrees as trained.

*Scaffold branch lenticels*.—About seven per nine square centimeters of growth.

*Scaffold branch lenticel shape*.—Generally flat.

*Scaffold branch lenticel length*.—From about 2.5 millimeters to about 3.5 millimeters with an average of about 3.0 millimeters.

*Scaffold branch lenticel width*.—From about 0.9 millimeters to about 1.6 millimeters with an average of about 1.3 millimeters.

*Scaffold branch lenticel color*.—From the White group (RHS N155D).

Two-year-old fruiting branches:

*Two-year-old branch diameter*.—From about 5.8 millimeters to about 9.9 millimeters with an average of about 7.9 millimeters.

*Two-year-old branch texture*.—Generally smooth.

*Two-year-old branch pubescence*.—None.

*Two-year-old branch color*.—From the Grey-Brown group (RHS N199D).

*Two-year-old branch lenticel numbers*.—Present and averaging about five lenticels per running centimeter of branch.

*Two-year-old branch lenticel shape*.—Generally round.

*Two-year-old branch lenticel diameter*.—From about 0.7 millimeters to about 1.1 millimeters.

*Two-year-old branch lenticel color*.—From the White group (RHS N155D).

Two-year-old branch spur development:

*Two-year-old branch spur length*.—From about 0.9 centimeters to about 3.6 centimeters.

*Two-year-old branch spur width*.—From about 3.8 millimeters to about 4.9 millimeters.

*Two-year-old branch bud shape*.—Generally elliptical in shape.

*Two-year-old branch spur bud length*.—From about 8.3 millimeters to about 10.7 millimeters with an average of about 9.4 millimeters.

*Two-year-old branch spur bud diameter*.—From about 4.0 millimeters to about 5.8 millimeters with an average of about 4.7 millimeters.

*Two-year-old branch tip bud length*.—From about 7.8 millimeters to about 9.2 millimeters with an average of about 8.6 millimeters.

*Two-year-old branch bud scale color*.—From the Greyed-Purple group (RHS N186C).

*Two-year-old branch spur pubescence*.—Light in density over about 60% of surface.

*Two-year-old branch spur pubescence color*.—From the White group (RHS N155D).

*Two-year-old branch crotch angle*.—From about 20 degrees to about 40 degrees.

2018 branches:

2018 *branch texture*.—Generally smooth.

2018 *branch length*.—From about 21.5 centimeters to about 69.5 centimeters with an average of about 48.0 centimeters.

2018 *branch diameter at midpoint*.—From about 6.0 millimeters to about 7.9 millimeters with an average of about 7.0 millimeters.

2018 *branch pubescence*.—Light in density over about 80% of surface.

2018 *branch pubescence color*.—From the White group (RHS N155D).

2018 *branch color*.—From the Brown group (RHS 200D).

2018 *branch lenticels*.—Present and averaging about 17 per running centimeter of branch.

2018 *branch lenticel shape*.—Generally round.

2018 *branch lenticel diameter*.—From about 0.6 millimeters to about 1.3 millimeters.

2018 *branch lenticel color*.—From the White group (RHS N155D).

2018 *branch internode length*.—From about 29.6 millimeters to about 41.8 millimeters with an average of about 35.9 millimeters.

Bloom (flowers):

*First bloom date*.—Apr. 27, 2018.

*Full bloom date*.—Apr. 30, 2018.

*Bud shape*.—Generally elliptical.

*Bud length*.—From about 8.3 millimeters to about 10.7 millimeters with an average of about 9.4 millimeters.

*Bud diameter*.—From about 4.0 millimeters to about 5.8 millimeters with an average of about 4.7 millimeters.

*Vegetative bud support size*.—About 4.5 millimeters.

*Bud color*.—From the Greyed-Purple group (RHS N186C).

*Number of blossoms per cluster*.—From about 4 to 6, mostly 5.

*Blossom size*.—Generally considered medium-large.

*Flower depth*.—About 11.2 millimeters.

*Diameter when fully open*.—From about 39.0 millimeters to about 49.0 millimeters with an average of about 43.8 millimeters.

*Petal count*.—About 5 per blossom.

*Petal shape*.—Generally oval with rounded tip.

*Petal arrangement*.—Free.

*Petal width*.—From about 13.7 millimeters to about 16.9 millimeters with an average of about 15.5 millimeters.

*Petal length*.—From about 17.3 millimeters to about 22.0 millimeters with an average of about 20.1 millimeters.

*Petal margin*.—Generally smooth.

*Petal color*.—Upper surface from the White group (RHS N155D). Undersurface highlights from the Red-Purple group (RHS N66D).

*Position of the stigmas relative to anthers*.—Anthers directly below and surrounding the stigma.

*Stamen number*.—From about 20 to about 22, mostly 20.

*Stamen filament length*.—From about 5.5 millimeters to about 7.6 millimeters with an average of about 6.8 millimeters.

*Stamen filament color*.—From the White group (RHS 155C).

*Stamen anthers shape*.—Generally kidney shaped.

*Stamen anthers width*.—From about 1.4 millimeters to about 2.0 millimeters with an average of about 1.7 millimeters.

*Stamen anthers length*.—From about 1.7 millimeters to about 2.4 millimeters with an average of about 2.1 millimeters.

*Stamen anthers color*.—From the Yellow-Orange group (RHS 18C).

*Stamen anthers pollen*.—Generally moderate in density.

*Stamen anthers pollen color*.—From the Greyed-Orange group (RHS 166C).

*Pistil length*.—From about 10.5 millimeters to about 11.9 millimeters with an average of about 11.2 millimeters. Styles are fussed an average of about 4.6 millimeters from base.

*Pistil color*.—From the Yellow-Green group (RHS 145A).

*Pubescence*.—No.

*Stigma number*.—About 5 or 6 per blossom.

*Stigma shape*.—Generally clubbed.

*Stigma color*.—From the Yellow-Orange group (RHS 20A).

*Sepal number*.—About 5 per blossom.

*Sepal shape*.—Generally lanceolate.

*Sepal shape at tip*.—Generally acuminate.

*Sepal shape at base*.—Generally truncate.

*Sepal length*.—From about 8.9 millimeters to about 12.2 millimeters with an average of about 10.5 millimeters.

*Sepal width*.—From about 3.6 millimeters to about 4.6 millimeters with an average of about 4.1 millimeters.

*Sepal margin*.—Generally smooth.

*Sepal color*.—From the Yellow-Green group (RHS 146B).

*Sepal pubescence*.—Moderate in density over 100% of both surface areas.

*Sepal pubescence color*.—From the White group (RHS 155C).

*Peduncle length*.—From about 18.8 millimeters to about 25.1 millimeters with an average of about 23.3 millimeters.

*Peduncle diameter at midpoint*.—From about 1.2 millimeters to about 1.7 millimeters with an average of about 1.6 millimeters.

*Peduncle color*.—From the Yellow-Green group (RHS 144A).

*Peduncle pubescence*.—Moderate in density over 100% surface area.

*Peduncle pubescence color*.—From the White group (RHS 155C).

*Thalmus depth*.—From about 4.1 millimeters to about 6.2 millimeters with an average of about 5.0 millimeters.

*Thalmus color*.—From the Yellow-Green group (RHS 147A).

*Thalmus pubescence*.—Moderate in density over 100% surface area.

*Thalmus pubescence color*.—From the White group (RHS 155C).

Leaves:

*Shape*.—Generally acute.

*Upper texture*.—Generally smooth and leathery.

*Lower texture*.—Generally smooth with veins protruding.

*Upper sheen*.—generally high gloss.

*Lower sheen*.—Generally medium gloss under the pubescence.

*Pubescence*.—Lightly moderate on about 100% of lower surface area.

*Pubescence color*.—From the White group (RHS 155C).

*Length*.—From about 9.4 centimeters to about 12.0 centimeters with an average of about 10.54 centimeters.

*Width*.—From about 5.3 centimeters to about 6.4 centimeters with an average of about 6.1 centimeters.

*Leaf profile cross-section*.—About 0.3 millimeters.

*Margin*.—Mostly crenate with occasional bi-serrate.

*Tip*.—Generally acuminate.

*Leaf blade tip length*.—About 0.8 centimeters.

*Base*.—Generally rounded (obtuse).

*Upper blade color*.—From the Green group (RHS 137A).

*Lower blade color*.—From the Green group (RHS 138B).

*Mid vein*.—Generally present on lower surface.

*Mid vein pubescence*.—Generally light on over 100% of surface.

*Mid vein pubescence color*.—White Group (RHS 155B).

*Mid vein diameter at midpoint*.—From about 1.2 millimeters to about 1.6 millimeters with an average of about 1.4 millimeters.

*Mid vein color*.—From the Green group (RHS 139D).

*Stipules*.—Present and about two per petiole.

*Stipules shape*.—Curved linear.

*Stipules length*.—From about 5.1 millimeters to about 11.9 millimeters with an average of about 9.2 millimeters.

*Stipules width*.—From about 1.4 millimeters to about 1.8 millimeters with an average of about 1.6 millimeters.

*Stipules color*.—Upper and Lower Stipules from the Green group (RHS 137A).

*Stipules pubescence*.—None.

*Petiole shallow grove upper surface*.—Generally present full length and from about 0.1 millimeters to about 0.2 millimeters in depth.

*Petiole length*.—From about 2.7 centimeters to about 3.7 centimeters with an average of about 3.2 centimeters.

*Petiole diameter at midpoint*.—From about 1.5 millimeters to about 1.9 millimeters with an average of about 1.7 millimeters.

*Petiole color*.—From the Green group (RHS 139D) with the basal end highlighted from the Greyed-Orange group (RHS N170D).

*Petiole pubescence*.—Generally light in density over all surface areas.

*Petiole pubescence color*.—From the White group (RHS 155C).

*Petiole attitude*.—Generally flat with blades rolled upwards from about 20 degrees to about 45 degrees with no drupe.

Fruit:

*Form*.—Considered mostly oblate, occasionally flat round.

*Size*.—Considered medium with normal crop level.

*Weight*.—About 295 grams.

*Equatorial diameter*.—From about 8.2 centimeters to about 9.2 centimeters with an average of about 8.8 centimeters.

*Axis diameter*.—From about 7.1 centimeters to about 8.3 centimeters with an average of about 7.8 centimeters.

*Stem*.—Generally not clubbed.

*Stem length*.—From about 17.5 millimeters to about 25.1 millimeters with an average of about 23.8 millimeters.

*Stem diameter at midpoint*.—From about 2.5 millimeters to about 3.3 millimeters with an average of about 2.8 millimeters.

*Stem color*.—From the Yellow-Green group (RHS 145D).

*Stem pubescence*.—Present in moderate density covering about 100% of surface.

*Stem pubescence color*.—From the Green-White group (RHS 157D).

*Stem cavity shape*.—Generally acute.

*Stem cavity lipped*.—No.

*Stem cavity russet*.—None observed.

*Stem cavity russet color*.—None observed.

*Stem cavity width*.—From about 29.2 millimeters to about 33.7 millimeters with an average of about 31.0 millimeters.

*Stem cavity depth*.—From about 15.1 millimeters to about 23.6 millimeters with an average of about 19.6 millimeters.

*Basin cavity ribbed*.—No.

*Basin cavity sides*.—Considered smooth, cone shaped.

*Basin cavity width*.—From about 27.2 millimeters to about 34.8 millimeters with an average of about 31.4 millimeters.

*Basin cavity depth*.—From about 9.9 millimeters to about 18.0 millimeters with an average of about 13.8 millimeters.

*Basin cavity eye*.—Considered mostly erect with occasional reflexed tips.

*Basin cavity eye pubescence*.—Downy present both upper and lower surface at moderately light density.

*Basin cavity eye pubescence color*.—From the White group (RHS 155D).

*Basin cavity eye shape*.—Considered closed with occasional reflexed tips.

*Skin appearance*.—Mostly flush with light molting and light bloom. No russet.

*Skin color*.—Flush area from the Red group (RHS 46A), Background from the Yellow group (RHS 8B).

*Skin thickness*.—Considered thin. About 0.1 millimeters.

*Skin texture*.—Generally smooth and melting.

*Skin lenticels*.—Generally not prominent.

*Skin lenticels shape*.—Generally round ranging from about 0.4 millimeters to about 0.6 millimeters in diameter.

*Skin lenticels number*.—About 6 per square centimeter.

*Skin lenticels color*.—From the Yellow group (RHS 8B).

*Core position*.—Considered distant from stalk.

*Core line position*.—Considered basal clapping.

*Core shape*.—Generally ovate.

*Core length*.—From about 30.0 millimeters to about 31.8 millimeters with an average of about 31.4 millimeters.

*Core diameter*.—From about 40.8 millimeters to about 43.8 millimeters with an average of about 42.6 millimeters.

*Cell tufted*.—No.

*Cell shape*.—Generally obovate.

*Cell length*.—From about 14.1 millimeters to about 16.5 millimeters with an average of about 15.1 millimeters.

*Cell width*.—From about 7.0 millimeters to about 10.7 millimeters with an average of about 8.8 millimeters.

*Cell wall-to-wall distance*.—From about 3.3 millimeters to about 4.3 millimeters with an average of about 3.8 millimeters.

*Tube shape*.—Considered cone shaped and closed to core.

*Tube stamen position*.—Considered basal.

*Tube axis*.—Considered abaxial and closed.

*Seed number*.—From about 1 to 2, mostly 2.

*Seed shape*.—Considered mostly acute with an occasional obtuse.

*Seed length*.—From about 8.1 millimeters to about 9.1 millimeters with an average of about 8.7 millimeters.

*Seed width*.—From about 5.4 millimeters to about 5.9 millimeters with an average of about 5.2 millimeters.

*Seed depth* (*wall to wall*).—From about 2.5 millimeters to about 3.2 millimeters with an average of about 2.9 millimeters.

*Seed color*.—From the Greyed-Orange group (RHS 177A).

*Flesh*.—Very firm, crisp, melting, and moderately subacid. No browning observed following 2 hours of cutting. Flavor is more honey-like than apple.

*Flesh color*.—From the Yellow group (RHS 11D).

*Aroma*.—Very light apple-like.

*Date of harvest maturity*.—Sep. 5, 2018.

*Maturity pressure*.—23.8 pounds.

*Maturity starch*.—3.0.

*Maturity soluble solids*.—15.4 brix %.

*Maturity malic acid*.—6.14 grams per liter.

*Maturity ph*.—3.84.

*Keeping quality*.—Up to about 6 months in common storage.

*Productivity*.—Considered moderate (from about 75 bins to about 80 bins per acre).

*Pollination*.—Any diploid apple of the same bloom season.

*Use*.—Desert. Excellent eating quality that is snappy, juicy, sweet with very good acid balance and melting skin.

*Disease and insect resistance*.—Considered to be susceptible to all insects and diseases found in the region of Central Washington. Fruit does not exhibit any physiological disorders on the tree nor during storage for the duration of normal storage lengths.

Although the new variety of apple tree possesses the described characteristics when grown under the ecological conditions prevailing in Vantage, Wash., in the south-central part of Washington state, it should be understood that variations of the usual magnitude and characteristics incident to changes in growing conditions, fertilization, pruning and pest control as well as horticultural management practices are to be expected.

What is claimed is:

1. A new and distinct variety of Apple tree named 'Regal D17-121' as herein illustrated and described.

* * * * *